US009737527B2

(12) United States Patent
Deng et al.

(10) Patent No.: US 9,737,527 B2
(45) Date of Patent: Aug. 22, 2017

(54) BIOPOLYMER DRUG LOADING METHOD

(71) Applicant: South Dakota Board of Regents, Pierre, SD (US)

(72) Inventors: Ying Deng, Vermillion, SD (US); Bo Yang, Vermillion, SD (US)

(73) Assignee: South Dakota Board of Regents, Pierre, SD (US)

( * ) Notice: Subject to any disclaimer, the term of this patent is extended or adjusted under 35 U.S.C. 154(b) by 0 days.

(21) Appl. No.: 15/065,723

(22) Filed: Mar. 9, 2016

(65) Prior Publication Data
US 2016/0263227 A1 Sep. 15, 2016

Related U.S. Application Data

(60) Provisional application No. 62/130,180, filed on Mar. 9, 2015.

(51) Int. Cl.
*A61K 31/155* (2006.01)
*A61K 31/4745* (2006.01)

(52) U.S. Cl.
CPC ........ *A61K 31/4745* (2013.01); *A61K 31/155* (2013.01)

(58) Field of Classification Search
CPC .......................... A61K 31/155; A61K 31/4745
See application file for complete search history.

(56) References Cited

U.S. PATENT DOCUMENTS 7,722,894 B2  5/2010  Wang et al.
8,236,350 B2  7/2012  Migneco et al.

*Primary Examiner* — Erich A Leeser
(74) *Attorney, Agent, or Firm* — Davis, Brown, Koehn, Shors & Roberts, P.C.; Sean D. Solberg

(57) ABSTRACT

A method of producing a drug-loaded Poly (Glycerol Sebacate) (PGS) comprising providing PGS; dissolving at least one drug in a solvent; incubating the PGS in the solvent; and evaporating the solvent.

14 Claims, 8 Drawing Sheets

Scale bar indicates 20 μm.

Fluorescence images of HGF-1 cells on the surface of (A) PGS, (B) B-PGS, (C) C-PGS and (D) BC-PGS after three days of seeding. Scale bar indicates 200 μm.

BIOPOLYMER DRUG LOADING METHOD

CROSS-REFERENCE TO RELATED APPLICATION(S)

This application claims the benefit of U.S. Provisional Application No. 62/130,180, filed on Mar. 9, 2015; which is incorporated herein by reference in its entirety

FIELD OF THE INVENTION

Disclosed herein are methods for improved drug loading of the bio-polymer Poly (Glycerol Sebacate) (PGS).

BACKGROUND OF THE INVENTION

Drug loaded bio-polymer implants provide advantages in many tissue engineering applications. For example, bio-polymer implants loaded with antibiotics can reduce risk of bacterial biofilm formation that can lead to implant site infection, immune reactions, implant failure, and bacteria-associated systematic problems. Poly (Glycerol Sebacate) (PGS) is a recently developed is a biocompatible, biodegradable, elastic polymer that has been widely tested for many tissue engineering applications. However, current PGS drug loading methods have a number of limitations. For example, past methods perform drug loading at the PGS pre-polymer stage. During the cross-linking process, residual solvent and loaded drug may affect the condensation proliferation process. This in turn may alter crosslinking speed and condition, crosslink drug and/or solvent into the polymer chain and alter drug formation, leading to reduced drug activity or to increased toxicity. Furthermore, the high heat required during crosslinking of pre-PGS can lead to degradation of many antimicrobial drugs. Accordingly, there is a need in the art for an improved method of PGS drug loading.

BRIEF SUMMARY OF THE INVENTION

Disclosed herein is a method of producing a drug-loaded Poly (Glycerol Sebacate) (PGS) comprising providing PGS, dissolving at least one drug in a solvent, incubating the PGS in the solvent; and evaporating the solvent. In certain aspects, the step of providing PGS further comprises synthesizing PGS by the steps of providing a mixture of gylceraol and sebacic acid, heating the mixture, polymerizing the mixture in a vacuum oven in N2 atmosphere to form a pre-polymer, cross-linking the PGS pre-polymer to form PGS, and balancing the PGS. According to certain aspects, the PGS is balanced in phosphate buffered saline (PBS). In yet further embodiments, PGS is cut into a desired form prior to incubation in the drug containing solvent.

DETAILED DESCRIPTION

Figure 1:
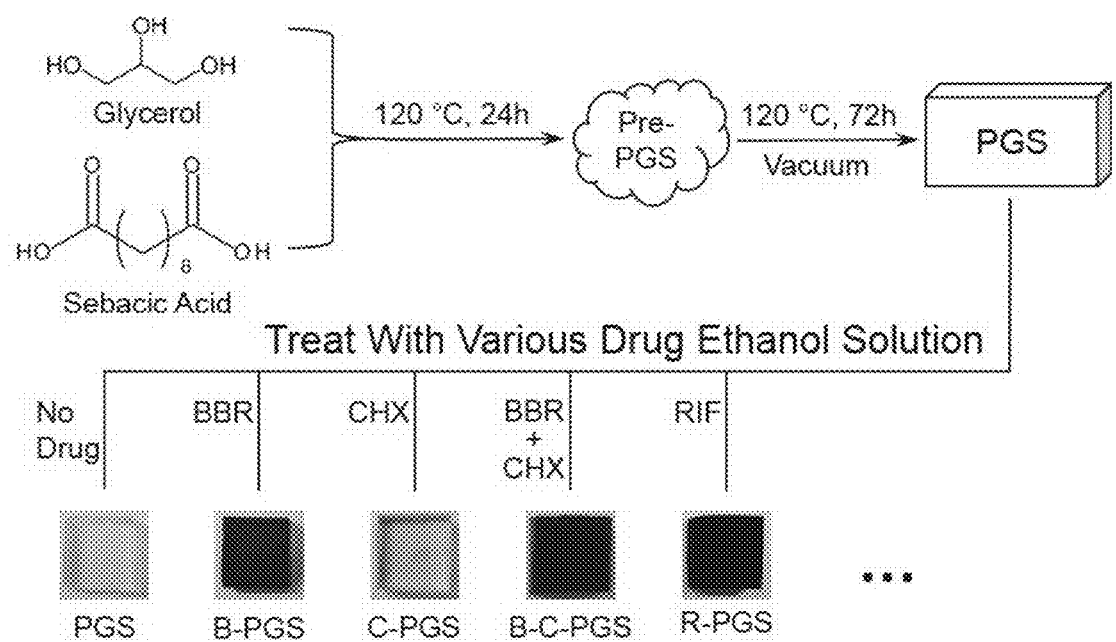
FIG. 1 is a flow chart of the disclosed drug loading method, according to certain embodiments.

Although the present invention has been described with reference to preferred embodiments, persons skilled in the art will recognize that changes may be made in form and detail without departing from the spirit and scope of the invention.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

Disclosed herein is a method of producing a drug-loaded Poly (Glycerol Sebacate) (PGS) comprising providing PGS, dissolving at least one drug in a solvent, incubating the PGS in the solvent; and evaporating the solvent. According to certain embodiments, providing PGS further comprises synthesizing PGS by the steps of providing a mixture of gylceraol and sebacic acid, heating the mixture, polymerizing the mixture in a vacuum oven in $N_2$ atmosphere to form a pre-polymer, cross-linking the PGS pre-polymer to form PGS, and balancing the PGS. According to certain embodiments, the PGS is balanced in phosphate buffered saline (PBS). In yet further embodiments, PGS is cut into a desired form prior to incubation in the drug containing solvent.

In certain exemplary embodiments, gylceraol and sebacic acid are added in approximately equimolar amounts.

In certain embodiments, the mixture is polymerized for about 24 hours. In further embodiments, the mixture is polymerized for between about 8 hours to about 36 hours.

In still further embodiments, the pre-PGS is crosslinked for about 72 hours. According to yet further embodiments, the pre-PGS is crosslinked from about 12 hours to about 144 hours.

According to certain embodiments, the solvent is a low toxicity solvent. In further embodiments, the solvent is ethanol. In yet further embodiments, ethanol is about 100% ethanol. In still further embodiments, the solvent is water. In further embodiments, the solvent is acetone, DMSO, or 2,2,2-trifluoroethanol. One skilled in the art will appreciate that other organic solvents may be used.

In certain embodiments, incubating the PGS in the solvent is performed between the temperatures of about −20° C. to about 100° C. In further embodiments, incubating the PGS in the solvent is performed between the temperatures of about −114° C. (melting point of ethanol) to 78° C. (boiling point of ethanol). In yet further embodiments, incubating the PGS in the solvent is performed at about 37° C.

According to certain embodiments, the at least one drug is an antimicrobial. In further embodiments, the antimicrobial is chlorhexidine. In yet further embodiments, the antimicrobial is berberine. In still further embodiments, the antimicrobial is berberine and chlorhexidine. In still further embodiments, the antimicrobial is selected from a group consisting of: penicillin, streptomycin, rifampicin, levofloxacin, tetracycline, erythromycin, and triclosan, According to further embodiments, the disclosed methods can be used to load other organic solvent and water soluble drug(s), including anti-cancer and anti-inflammatory drugs.

Disclosed herein is a drug-loaded PGS product prepared by a process comprising the steps of providing PGS; dissolving at least one drug in a solvent; incubating the PGS in the solvent; and evaporating the solvent. According to certain embodiments, providing PGS further comprises the steps of providing a mixture of gylceraol and sebacic acid; heating the mixture; polymerizing the mixture in a vacuum oven in $N_2$ atmosphere to form a pre-polymer; cross-linking the PGS pre-polymer to form PGS; and balancing the PGS.

According to certain embodiments, the at least one drug of the product produced by the disclosed process is an antimicrobial. In further embodiments, the antimicrobial is chlorhexidine. In yet further embodiments, the antimicrobial is berberine. In still further embodiments, the antimicrobial is berberine and chlorhexidine. In still further embodiments, the antimicrobial is selected from a group consisting of: penicillin, streptomycin, rifampicin, levofloxacin, tetracycline, erythromycin, and triclosan, According to further embodiments, the disclosed methods can be used to load other organic solvent and water soluble drug(s), including anti-cancer and anti-inflammatory drugs.

According to certain embodiments, the product disclosed herein can be used for a variety of tissue engineering purposes. For example, according to certain embodiments, the disclosed drug-loaded PGS product can be used for cardiac tissue engineering, vascular tissue engineering, cartilage tissue engineering, retinal tissue engineering and nerve tissue engineering. Depending on loaded drug(s), the drug loaded PGS can exhibit multiple biological activities while retaining its original mechanical and biological properties.

In certain embodiments, drug loading of PGS according to the disclosed process does not affect the mechanical properties of PGS. For example, PGS elasticity of drug loaded PGS, according to certain embodiments, is substantially similar to non-drug loaded PGS.

According to still further embodiments, the disclosed drug-loaded PGS product is capable of sustained drug release. In still further embodiments, the disclosed drug-loaded PGS performs sustained drug release for at least 60 days.

According to certain exemplary embodiments, the disclosed drug-loaded PGS product has antimicrobial properties. In still further embodiments, the disclosed drug-loaded PGS product reduces bacterial adhesion. In yet further embodiments, the disclosed drug-loaded PGS product has high compatibility with human cell types. In still further embodiments, the disclosed drug-loaded PGS product provides an effective treatment for periodontal disease when administered as a dental implant.

Experimental

The following examples are put forth so as to provide those of ordinary skill in the art with a complete disclosure and description of certain examples of how the compounds, compositions, articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Materials and Methods

*S. aureus* (ATCC 6538), *E. coli* (ATCC 15597) and Methicillin-resistant *Staphylococcus aureus* (MRSA, ATCC BAA-811) were purchased from American Type Culture Collection (ATCC, Manassas, Va.). Human gingival fibroblast (HGF-1) were purchased from American Type Culture Collection (ATCC, Manassas, Va.). All reagents used in our work including glycerol, sebacic acid, berberine chloride, chlorhexidine and ethanol were from Sigma-Aldrich (Sigma-Aldrich, St Louis, Mo.) unless otherwise specified.

Synthesis of PGS

Poly (Glycerol Sebacate) (PGS) was synthesized following the disclosed method, shown schematically in FIG. 1. Briefly, equimolar of glycerol and sebacic acid were melted down and mixed evenly. The mixture was then put into vacuum oven (Fisher Isotemp Vacuum Oven Model 281A, Fisher Scientific, Waltham, Mass.) at 120° C. in N2 atmosphere for 24 hours for the synthesis of PGS pre-polymer (pre-PGS). Pre-PGS was then cross-linked at 120° C. under vacuum for 72 hours to make the 3-D cross-linked PGS elastic polymer. Synthesized PGS was then cut into 10 mm×10 mm×4 mm cubes and balanced in phosphate buffered saline (PBS) for 3 days before use.

Swelling Drug Loading

Due to its unique 3-D structure, PGS does not get dissolved in most solvents. However, it swells in many organic solvents, and that property can be used for drug loading. As will be appreciated by those skilled in the art, many drugs can be loaded into PGS using various solvents (organic solvents or water). In the instant examples, berberine and chlorhexidine were selected as exemplary drugs and ethanol as an exemplary drug-loading solvent. One skilled in the art will appreciate that other drugs and solvents can be used.

Selected drugs (individually and together) were dissolved 100% ethanol to make a saturated solution. PGS cubes were then put into saturated drug/ethanol solution for swelling and drug loading for 2 days. Drug loaded PGS cubes were slowly dried and cleaned afterward. In the present example, berberine loaded PGS (B-PGS) cubes, chlorhexidine loaded PGS (C-PGS) cubes, and berberine-chlorhexidine loaded PGS (B-C-PGS) cubes were prepared with saturated drug ethanol solution respectively and PGS cubes treated with pure 200 ethanol were employed as control.

PGS Swelling Test

PGS was synthesized, buffered and cut into 10 mm×10 mm×4 mm cubes as mentioned above. PGS cubes were weighted (W_0) before swelling test. Ethanol and acetone were selected for swelling test because they are commonly used, less toxic class 3 solvents in pharmaceutical industry. PGS cubes were weighted again (W_1) after 48 hours drug loading treatment. The swelling behavior ($SB_w(\%)$) was calculated based on weight change with the following equation:

$$SB_w(\%) = \frac{W_1 - W_0}{W_0} \times 100\%$$

PGS swelling behavior in di water and phosphate buffered saline (PBS) were also tested for reference.

Drug Loading and Release Test

Drug loaded PGS cubes were placed into 2,2,2-trifluoroethanol (TFE) for three days for a complete release. Berberine concentration was determined by measuring the optical density of the supernatant at 344 nm using a microplate reader (Tecan infinite M200, Tecan Group Ltd. Männedorf, Switzerland). Two drug loading parameters—temperature and ethanol/water ratio were optimized for higher drug loading efficiency. All tests were performed at 37° C. with 100% ethanol unless otherwise specified.

Sterile PBS was used for drug release test. One cube of treated PGS sample was placed into a glass vial containing 10 ml sterile PBS. The glass vial was then placed into a mechanical to test the drug releasing property at 37° C., 150 rpm. Sterile PBS was changed daily and released drug was measured using the same method as in drug content test.

Mechanical Test

Synthesized PGS were cut into 50 mm×10 mm×4 mm strips. Drug(s) were loaded into PGS strips using the same method while an untreated group was prepared without any drug loading treatments. For the mechanical test, five groups of samples (PGS, B-PGS, C-PGS, BC-PGS and untreated) were mounted on the sample loader of MTS insight electromechanical testing system (MTS systems corporation, Eden Praire, Minn.). Young's modulus and strain at break were measured by running MTS tensile method with five groups of samples.

Surface Wettability Test

Surface wettability was determined by contact angle goniometry by using VCA optima contact angle analysis system (AST products, Inc., Billerica, Mass.). In this test, one drop (2 μL) of distilled water was dropped onto the horizontal surface of a sample cube. Photos were taken using the contact angle analysis system after 1 minute and contact angles were measured with its software workstation.

Antimicrobial Test

General antimicrobial test was taken following ASTM standard E2149-10. *E. coli* was cultured in LB broth (Lennox, Fisher Scientific, Pittsburgh, Pa.) overnight. *S. aureus* and MRSA was cultured in tryptic soy broth (Fluka analytical, Sigma-Aldrich, St Louis, Mo.) overnight. All bacteria were grown to OD470=0.30~0.35 and was further diluted 100 times with PBS. PGS, B-PGS, C-PGS and BC-PGS cubes were put into 20 ml diluted bacteria solution and shaken vigorously in an isotemp shaker (MAXQ 4450, Thermo Scientific, Waltham, Mass.) at 37° C. The colony formation unit (CFU) of the supernatant was tested after 1 and 4 hours to determine the antimicrobial activity of four groups of samples.

Bacteria Adhesion Test

Gram-positive bacteria *S. aureus* (ATCC 6538) and gram negative bacteria *E. coli* (ATCC 15597) were used for bacteria adhesion test. *S. aureus* was grown in tryptic soy broth, and *E. coli* was grown in Luria-Bertani (LB) broth overnight ahead of use. Both bacteria were then diluted to 105 CFU/ml using the corresponding broth. Four groups of PGS cubes (PGS, B-PGS, C-PGS and B—C-PGS) were immersed in 20 ml of diluted bacteria broth individually and cultured at 37° C. for 3 days.

Samples were taken out and washed thoroughly with PBS after 3 days of culture. To test the bacteria adhesion, samples were fixed in 2.5% glutaraldehyde for 2 h and dehydrated with a series of ethanol solution (70%, 80%, 90%, and 100%) for 10 minutes each. Samples were then dried and coated with 10 nm gold with a sputter coater (Cressington 108, Cressington Scientific Instruments Ltd. Watford, UK) and observed with a Scanning Electron Microscope (SEM) (FEI Quanta 450, FEI Company, Hillsboro, Oreg.).

Cell Compatibility Test

Human gingival fibroblast cells (HGF-1, ATCC® CRL-2014™) were used for the cell compatibility assay. HGF-1 cells were cultured in DMEM/High Glucose supplemented with 1% non-essential amino acids (Fisher Scientific, Pittsburgh, Pa.), 1% antibiotics (Fisher Scientific, Pittsburgh, Pa.), and 10% fetal bovine serum (Sigma-Aldrich, St Louis, Mo.). Four groups of samples were sterilized by UV and were balanced in cell culture media for 7 days in a 24 well plate before the test. HGF-1 cells were then seeded onto the surface of the membranes at a concentration of 100,000 cells per well. PGS cubes were taken out and fixed with 2.5% glutaraldehyde at 4° C. overnight. Samples were then permeabilized with 0.5% triton X-100 for 10 minutes at room temperature. Permeabilized cells were stained with 100 nM rhodamine phalloidin (Molecular Probes Life Technologies, Eugene, Oreg.) in the dark at room temperature for 30 minutes. After rhodamine phalloidin stain, samples were treated with 0.3% (w/w) Sudan Black for 30 minutes to reduce background emission. Fluorescence images were taken by Axiovert 200 fluorescence microscope (Axiovert 200, Carl Zeiss AG, Jena, Germany).

Statistical Analysis

All quantitative tests were carried out with three parallel samples, with results presented in the form of mean±standard deviation (S.D.) unless otherwise specified. The statistical significance of the data obtained was analyzed by one-way ANOVA. Probability values of $p<0.05$ were interpreted as statistically significant.

Results

PGS Swelling and Drug Loading

Figure 2:
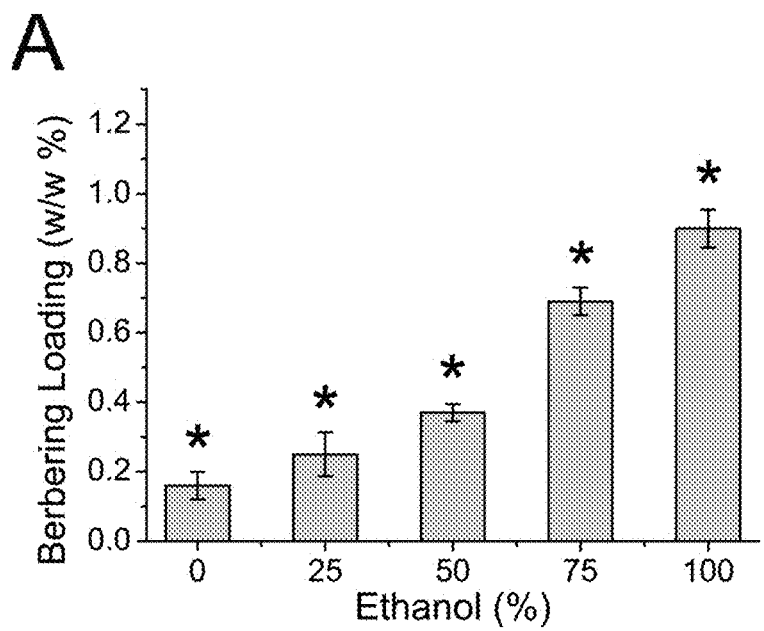
FIG. 2 shows PGS drug loading efficiency under various ethanol concentrations (A) and temperatures (B), according to certain embodiments.
Figure 2:
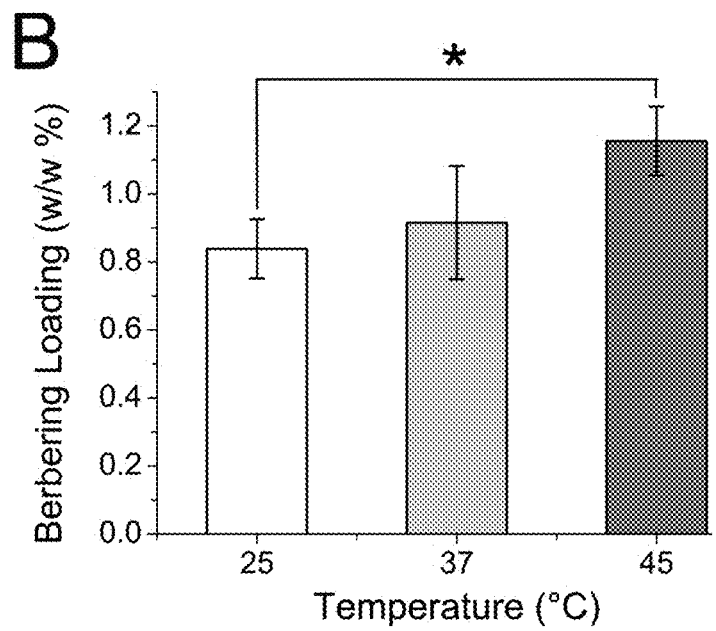

The synthesized PGS is a transparent, elastic polymer. PGS is able to swell in many organic solvents and water (Table 1). Ethanol was chosen as drug loading solvent because: 1) it has low toxicity; 2) the two model drugs used—berberine and chlorhexidine—both have good solubility in ethanol; and 3) PGS can maintain its surface morphology after ethanol treatment. As shown in FIG. 2 (panel A), the solvent selection test showed that berberine loading efficiency decreases with the decrease of ethanol composition in the solvent system and 100% ethanol shows highest berberine loading efficiency.

TABLE 1

| Solvent | Water | PBS | Ethanol | Acetone |
|---|---|---|---|---|
| Swelling | 3.82% ± 0.25% | 3.41% ± 0.19% | 55.22% ± 0.51% | 113.98% ± 1.95% |

As shown in FIG. 2 (panel B), increasing temperature is also able to increase berberine loading efficiency. However, drugs can be unstable in high temperature and 37° C. was chosen as drug loading temperature as a balance of sufficient drug loading efficiency and drug stability.

Using tested PGS swelling behavior ($SB_w$), drug loading concentration ($c_l$) and solvent density ($\rho$), expected drug loading (EDL (w/w)) can be calculated with the following concentration:

$$EDL(w/w) = \frac{SB_w}{\rho} \times c_l \times 100\%$$

The expected drug loading is calculated by assuming that drugs and material have no interaction while the only mechanism for drug loading is the swelling process. However, as shown in Table 2, tested drug loading is higher than expected drug loading for both berberine and chlorhexidine. This indicates that PGS produces a positive effect on the berberine and chlorhexidine loading process.

TABLE 2

Expected and actual drug loading efficiency of B-PGS and C-PGS

|  | Expected Drug Loading | Tested Drug Loading | Drug Loading Efficiency |
|---|---|---|---|
| Berberine in B-PGS | 0.402% | 0.699% | 173.71% |
| Chlorhexidine in C-PGS | 0.019% | 0.042% | 221.49% |

Releasing Behavior of Drug Loaded PGS

Figure 3:
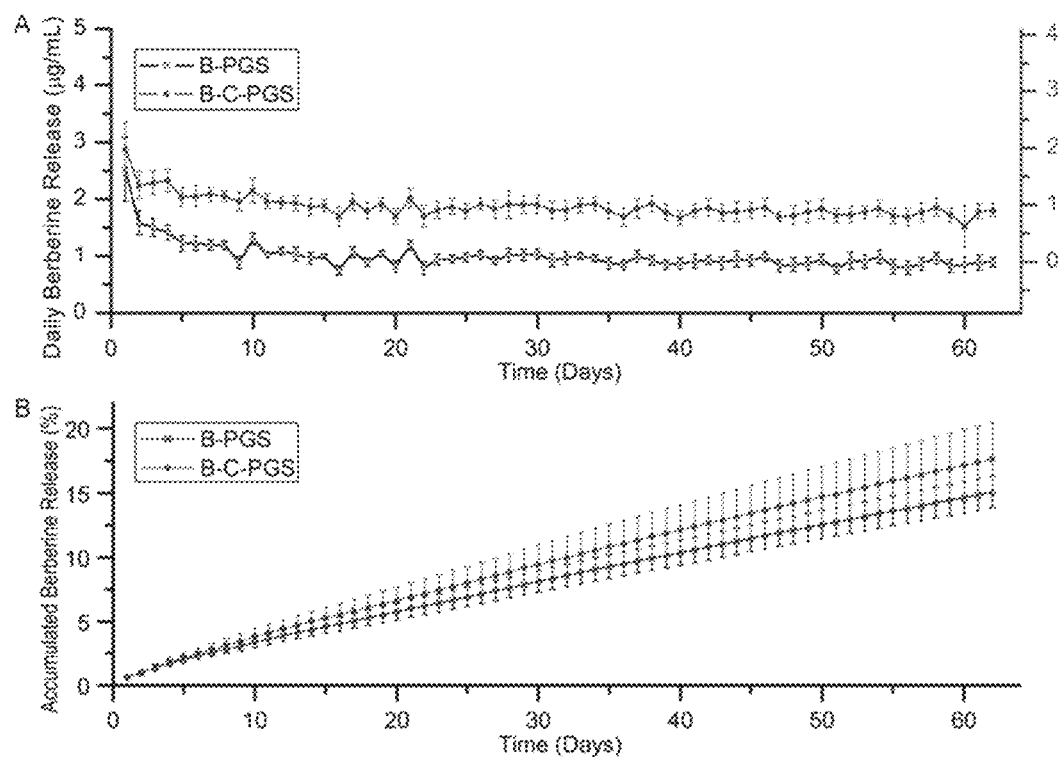
FIG. 3 shows daily (A) and accumulated (B) release profile of Berberine in B-PGS and BC-PGS, according to certain embodiments.

Drug release was assessed in sterile PBS to avoid PGS degradation. The daily and accumulated release curve of berberine in B-PGS and BC-PGS is shown on FIG. 3. 15% of berberine was released after 62 days with a stable daily release concentration of around 1 µg/ml. Chlorhexidine release concentration was too low to be detected with the detection method (<5 µg/ml). The results indicate that drug-loaded PGS performed sustained release of the drugs.

Mechanical Test

Figure 4:
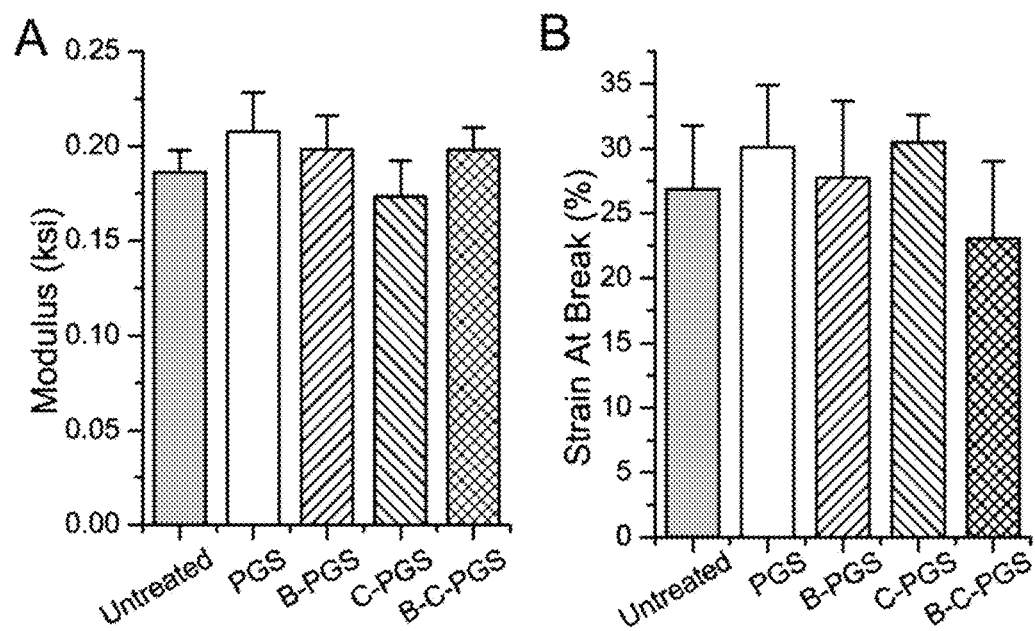
FIG. 4 shows Young's modulus (A) and strain at break (B) of untreated PGS (Untreated), drug loading treated PGS (PGS), berberine loaded PGS (B-PGS), chlorhexidine loaded PGS (C-PGS) and berberine-chlorhexidine loaded PGS (BC-PGS), according to certain embodiments.

One important property of PGS is its elastic property. To determine whether drug loading affected mechanical properties of PGS, an elongation test was performed. As shown in FIG. 4, PGS (drug loading treated), B-PGS, C-PGS and BC-PGS showed no significant difference compared with untreated (untreated PGS) samples as measured by Young's modulus (FIG. 4, panel A) and strain at break (FIG. 4, panel B). This result indicated the disclosed swelling drug loading method and loaded drug(s) did not change the mechanical property of original PGS.

Surface Wettability Test

Figure 5:
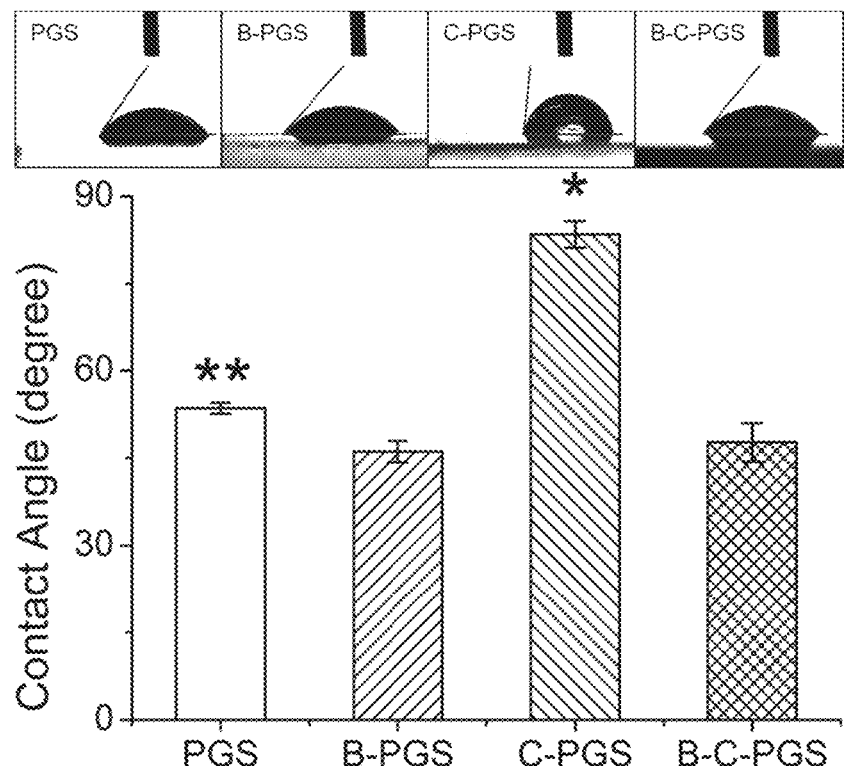
FIG. 5 shows surface wettability data for PGS, B-PGS, C-PGS and B—C-PGS, according to certain embodiments.

Material surface wettability is an important property for tissue engineering. Surface wettability of PGS, B-PGS, C-PGS and BC-PGS was tested using water contact angle test, as shown in FIG. 5. The contact angle of PGS is 53.5°, which is suitable for cell attachment. Hydrophilic drug berberine decreased water contact angle to 46°. This indicated an improved surface wettability and can have some beneficial in tissue engineering. On the other side, hydrophobic drug chlorhexidine increase water contact angle to 83.5°, making the surface of C-PGS more hydrophobic. Interestingly, when hydrophilic drug berberine and hydrophobic drug chlorhexidine loaded together, BC-PGS performed a similar water contact angle (47.7°) as B-PGS.

Antimicrobial Test

Figure 6:
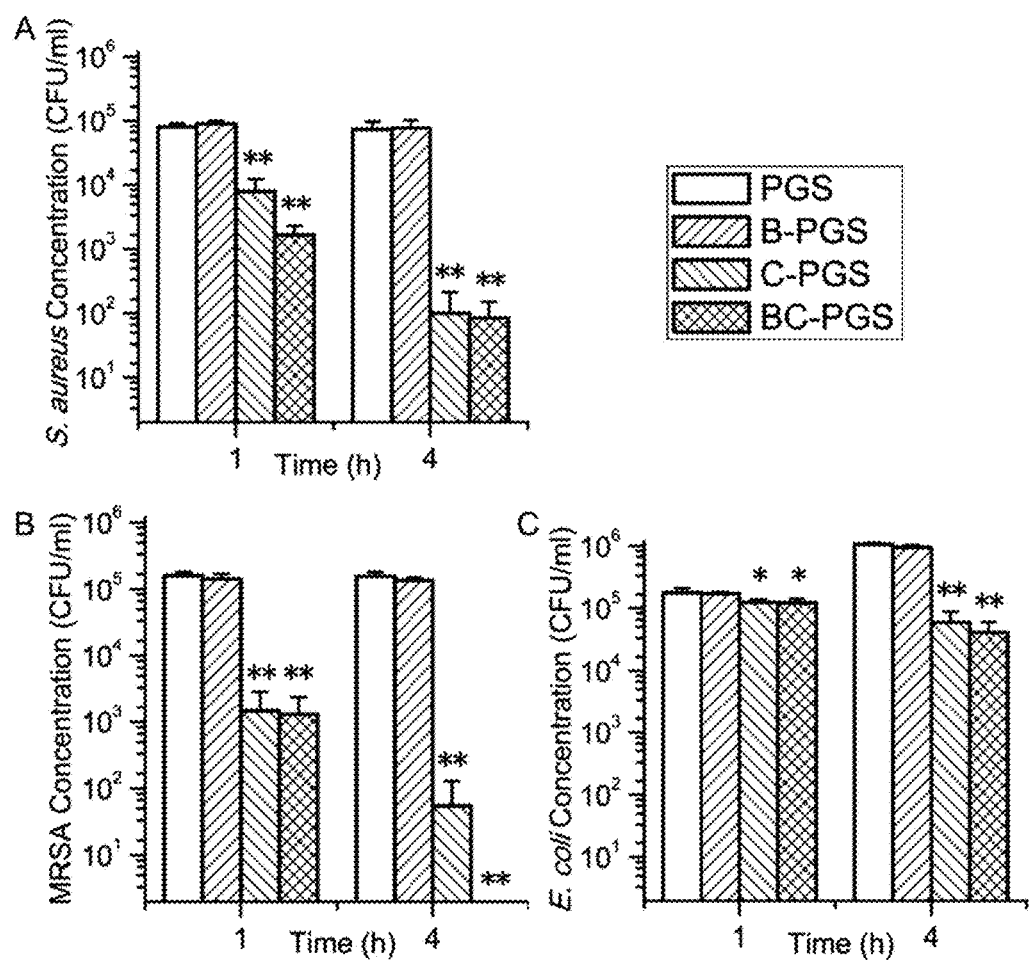
FIG. 6 shows antimicrobial data for S. aureus (A), MRSA (B) and E. coli (C), according to certain embodiments.

FIG. 6 shows the result of general antimicrobial test against of S. aureus (panel A), MRSA (panel B) and E. coli (panel C) for PGS, B-PGS, C-PGS and BC-PGS. (Star sign indicates the marked group has significant difference to PGS group of each time point. * $p<0.05$, ** $p<0.01$.) Chlorhexidine loaded groups (C-PGS and BC-PGS) showed good antimicrobial effect against typical gram-positive bacteria S. aureus, typical gram-negative bacteria E. coli and typical antibiotic-resistant bacteria MRSA.

C-PGS killed 99.86% S. aureus, 94.36% E. coli, and 99.96% MRSA while BC-PGS killed 99.88% S. aureus, 96.13% E. coli and 100% MRSA after 4 hours of incubation. B-PGS does not show any significant antimicrobial effect in general antimicrobial test. However, in most test groups, BC-PGS showed higher antimicrobial effect than C-PGS.

Bacteria Adhesion of Drug Loaded PGS

Figure 7:
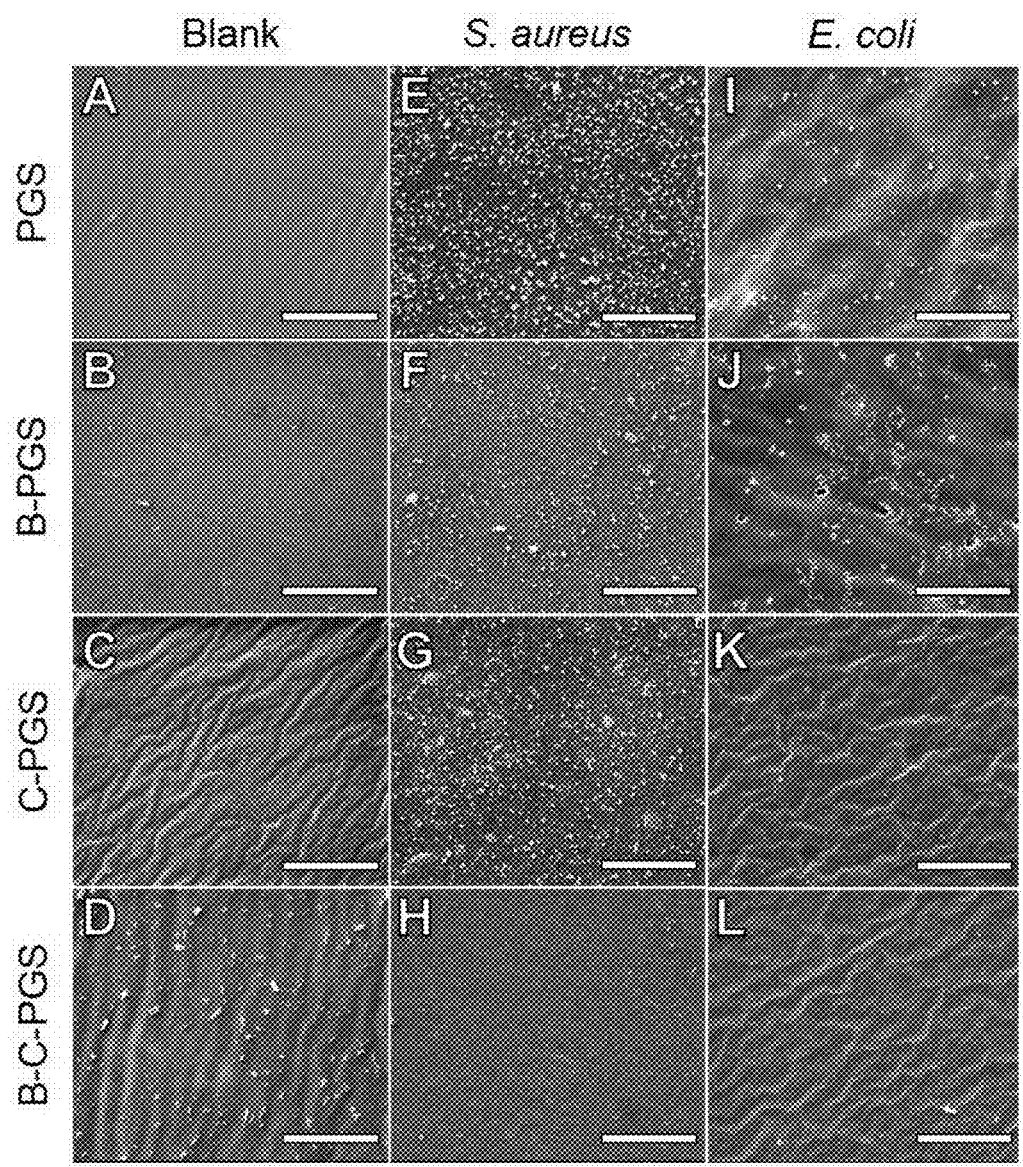
FIG. 7 shows SEM images of sample surfaces before (A~D) and after culture with S. aureus (E~H) and E. coli (I~L) for 3 days, according to certain embodiments.

As shown in FIG. 7, SEM images showed that PGS samples had a smooth, clear surface with occasionally micro-scaled crests and troughs (FIG. 7 panel C) as well as deposited drug crystal (FIG. 7 panel D).

After incubating with S. aureus for 3 days, significant amounts of bacteria was observed on the surface of PGS (FIG. 7, panel E) while fewer bacteria was found on C-PGS (FIG. 7, panel G). Interestingly, although B-PGS had weaker antimicrobial effect than C-PGS, fewer bacteria can be found on its surface (FIG. 7, panel F). In addition, very few bacteria were observed on the surface of B—C-PGS (FIG. 7, panel H), indicating an excellent anti-adhesion property against S. aureus.

Different result was observed on the E. coli co-cultured groups. The attached bacteria concentration was less than S. aureus on all sample surfaces after 3-day incubation. C-PGS group showed better anti-adhesion effect than B-PGS group against E. coli. Moreover, very few bacteria were found on the surface of B-C-PGS.

Cell Compatibility Test

Figure 8:
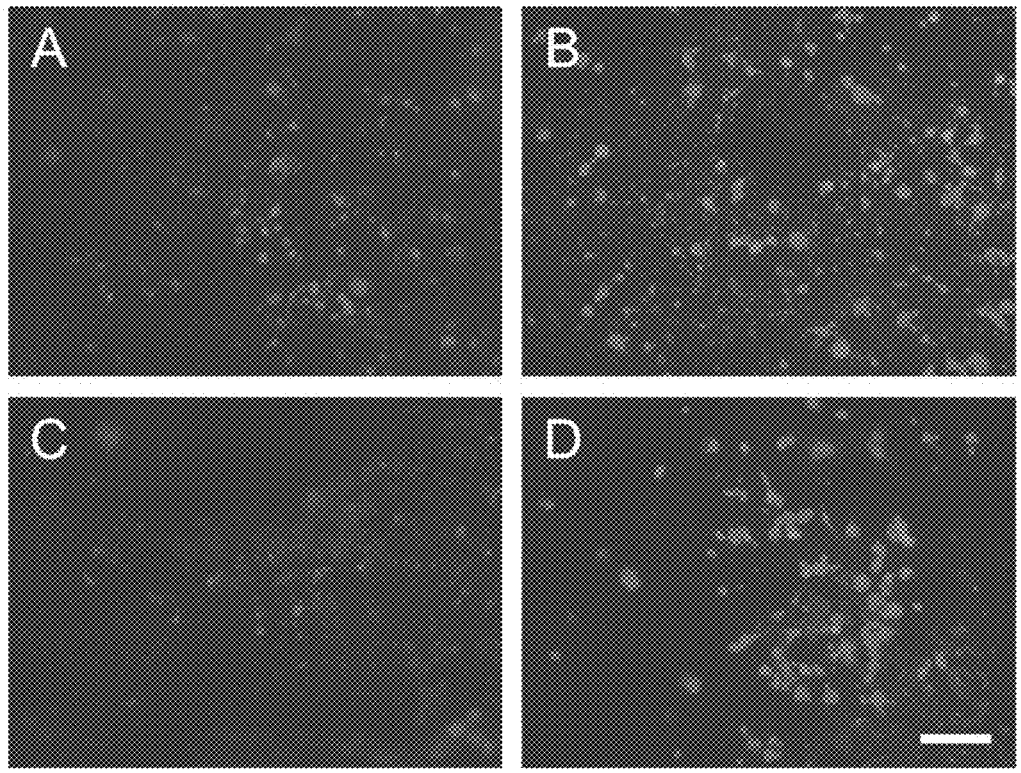
FIG. 8 shows fluorescence images of HGF-1 cells on the surface of (A) PGS, (B) B-PGS, (C) C-PGS and (D) BC-PGS after three days of seeding, according to certain embodiments.

Human gingival fibroblast (HGF-1) was used because it is the most abundant cell in periodontal soft tissue. FIG. 6 shows the fluorescence images of HGF-1 cell grown on sample surfaces after 3 days. Compared to the PGS group (FIG. 8, panel A), more cells were found on the surface of B-PGS (FIG. 8, panel B) and BC-PGS (FIG. 8, panel D). While fewer cells were found on the surface of C-PGS (FIG. 8, panel C). This shows berberine loaded PGS groups have improved cell compatibility with HGF-1.

Although the present invention has been described with reference to preferred embodiments, persons skilled in the art will recognize that changes may be made in form and detail without departing from the spirit and scope of the invention.

What is claimed is:
1. A method of producing a drug-loaded Poly (Glycerol Sebacate) (PGS) comprising:
   a. providing PGS;
   b. dissolving at least one drug in a solvent;
   c. incubating the PGS in the solvent; and
   d. evaporating the solvent.
2. The method of claim 1, wherein providing PGS further comprises:
   a. providing a mixture of gylceraol and sebacic acid;
   b. heating the mixture;
   c. polymerizing the mixture in a vacuum oven in $N_2$ atmosphere to form a pre-polymer;
   d. cross-linking the PGS pre-polymer to form PGS; and
   e. balancing the PGS.
3. The method of claim 2, wherein the mixture is polymerized for about 24 hours.
4. The method of claim 2, wherein the pre-PGS is cross-linked for about 72 hours.
5. The method of claim 1, wherein the solvent is a low toxicity solvent.
6. The method of claim 5, wherein the solvent is ethanol.
7. The method of claim 1, wherein the incubating the PGS in the solvent is performed at between the temperatures of from about −20° C. to about 100° C.
8. The method of claim 7, wherein the incubating the PGS in the solvent is performed at about 37° C.
9. The method of claim 1, wherein the solvent is evaporated at room temperature for at least 7 days.
10. The method of claim 1, wherein the at least one drug is an antimicrobial.
11. The method of claim 10, wherein the antimicrobial is chlorhexidine.
12. The method of claim 10, wherein the antimicrobial is berberine.
13. The method of claim 10, wherein the antimicrobial is berberine and chlorhexidine.
14. The method of claim 10, wherein the antimicrobial is selected from a group consisting of: penicillin, streptomycin, rifampicin, levofloxacin, tetracycline, erythromycin, and triclosan.

* * * * *